United States Patent
Lichter et al.

(10) Patent No.: US 9,867,286 B2
(45) Date of Patent: Jan. 9, 2018

(54) CIRCUIT BOARD COMPRISING AN INSULATING DIAMOND MATERIAL

(71) Applicants: National ICT Australia Limited, Eveleigh, NSW (AU); THE UNIVERSITY OF MELBOURNE, Melbourne, Victoria (AU)

(72) Inventors: Samantha Lichter, Eveleigh (AU); Nicholas Apollo, Melbourne (AU); David Garrett, Melbourne (AU); Kumaravelu Ganesan, Melbourne (AU); Hamish Meffin, Eveleigh (AU); Steven Prawer, Melbourne (AU)

(73) Assignees: National ICT Australia Limited, Eveleigh (AU); The University of Melbourne, Melbourne (AU)

( * ) Notice: Subject to any disclaimer, the term of this patent is extended or adjusted under 35 U.S.C. 154(b) by 0 days.

(21) Appl. No.: 14/901,008

(22) PCT Filed: Jun. 25, 2014

(86) PCT No.: PCT/AU2014/000660
§ 371 (c)(1),
(2) Date: Dec. 22, 2015

(87) PCT Pub. No.: WO2014/205489
PCT Pub. Date: Dec. 31, 2014

(65) Prior Publication Data
US 2016/0157342 A1    Jun. 2, 2016

(30) Foreign Application Priority Data
Jun. 25, 2013   (AU) ................................ 2013902332

(51) Int. Cl.
*A61N 1/375* (2006.01)
*H05K 1/03* (2006.01)
(Continued)

(52) U.S. Cl.
CPC ....... *H05K 1/0306* (2013.01); *A61N 1/36046* (2013.01); *H01L 23/053* (2013.01);
(Continued)

(58) Field of Classification Search
CPC ........ H05K 1/0306; H05K 1/09; H05K 1/111; H05K 3/0044; H05K 3/107; H05K 3/146;
(Continued)

(56) References Cited

U.S. PATENT DOCUMENTS 6,220,765 B1 * 4/2001 Tatoh .................. H01L 31/0203
257/E31.117
6,607,673 B2 * 8/2003 Fujishima ............. C23C 16/045
216/11

(Continued)

FOREIGN PATENT DOCUMENTS

WO    WO 2012/162743 A1    12/2012

OTHER PUBLICATIONS

International Search Report dated Aug. 19, 2014 in International Application No. PCT/AU2014/000660, filed Jun. 25, 2014.
(Continued)

*Primary Examiner* — Michael Carey
(74) *Attorney, Agent, or Firm* — Knobbe, Martens, Olson & Bear LLP

(57) ABSTRACT

A circuit board is described. The circuit board comprises an electrically insulating diamond material having a surface. The electrically insulating diamond material has at least one recess extending into only a portion of a thickness of the electrically insulating diamond material from the surface of the electrically insulating diamond material. The circuit board also comprises an electrically conductive material located at least partially within the recess.

20 Claims, 5 Drawing Sheets

(51) Int. Cl.
| | |
|---|---|
| H01L 23/14 | (2006.01) |
| H01L 23/053 | (2006.01) |
| H05K 1/09 | (2006.01) |
| H05K 3/10 | (2006.01) |
| A61N 1/36 | (2006.01) |
| H05K 1/11 | (2006.01) |
| H05K 3/00 | (2006.01) |
| H05K 3/14 | (2006.01) |
| A61N 1/05 | (2006.01) |

(52) U.S. Cl.
CPC ............... *H01L 23/14* (2013.01); *H05K 1/09* (2013.01); *H05K 1/111* (2013.01); *H05K 3/0044* (2013.01); *H05K 3/107* (2013.01); *H05K 3/146* (2013.01); *A61N 1/0543* (2013.01); *H01L 2224/14* (2013.01); *H01L 2224/17* (2013.01); *H01L 2924/0002* (2013.01); *H05K 2201/0323* (2013.01); *H05K 2201/0376* (2013.01)

(58) Field of Classification Search
CPC ... H05K 2201/0323; H05K 2201/0376; A61N 1/36046; A61N 1/0543; H01L 23/053; H01L 23/14; H01L 2224/14; H01L 2224/17; H01L 2924/0002

USPC ...... 607/116, 115, 2; 600/300; 427/2.1, 2.11, 427/2.24, 2.12
See application file for complete search history.

(56) References Cited

U.S. PATENT DOCUMENTS

| | | | |
|---|---|---|---|
| 7,127,286 B2 | 10/2006 | Mech et al. | |
| 2002/0120296 A1* | 8/2002 | Mech | A61K 9/0009 607/2 |
| 2005/0224806 A1* | 10/2005 | Gluche | H01L 28/22 257/77 |
| 2007/0295973 A1* | 12/2007 | Jinbo | H01L 27/1214 257/88 |
| 2012/0256704 A1* | 10/2012 | Johnson | A61N 1/3718 333/185 |

OTHER PUBLICATIONS

Hadjinicolau et al., "Electrical stimulation of retinal ganglion cells with diamond and the development of an all diamond retinal prosthesis," *Biomaterials* vol. 33, issue 24, pp. 5812-5820 (2012).

* cited by examiner

CIRCUIT BOARD COMPRISING AN INSULATING DIAMOND MATERIAL

FIELD OF THE INVENTION

The present invention relates to a circuit board comprising an insulating diamond material, and relates particularly, though not exclusively, to a circuit board for an implantable medical device.

BACKGROUND OF THE INVENTION

Medical devices that include electronic components are frequently implanted into the human body. Such medical devices include cochlear implants, pacemakers, retinal prostheses and other devices. It is important that the electronic components of such medical devices are protected from fluid exposure.

It has recently been proposed to form portions of such implantable devices from a diamond material as diamond is a biocompatible and strong material that is impermeable to fluid ingress. The present invention provides further improvement.

SUMMARY OF THE INVENTION

The present invention provides in a first aspect a circuit board comprising:
  an electrically insulating diamond material having a surface;
  at least one recess extending into only a portion of a thickness of the electrically insulating diamond material from the surface of the electrically insulating diamond material; and
  an electrically conductive material located at least partially within the recess.

Throughout this specification the term "diamond material" is used for films or bulk materials of crystalline diamond material, poly-crystalline diamond material, nano-crystalline diamond material and also for diamond-like materials including diamond glassy carbon and diamond-like carbon materials.

It will be appreciated that the circuit board is formed such that the electrically conductive material within the at least one recess does not extend through to a surface of the electrically insulating diamond material opposite the surface on which the recess is provided. The electrically conductive material extends only partially into the thickness of the electrically insulating diamond material, for example up to 10%, 20%, 30%, 40%, 50%, 60%, 70%, 80% or 90% of the thickness of the electrically insulating diamond material.

Further, it will be appreciated that the conductive material may be contained such that conductive material of adjacent recesses do not contact at a region of the electrically insulating diamond material that lies beyond the adjacent recesses. For example, the conductive material may be contained entirely within the at least one recess.

Conventional electrically conductive wire portions that may be formed on the surface of insulating diamond material are often relatively fragile. However, the conductive material of the circuit board in accordance with embodiments of the present invention may be at least partially embedded in the insulating diamond material. This reduces fragility of the electrically conductive material and also reduces space requirements, which is of particular advantage when the circuit board forms a portion of an implantable medical device that should be as small as possible.

In one embodiment the at least one recess extends along a length of the surface of the electrically insulating diamond material. The recess, or at least one of the recesses, and the electrically conductive material may be elongated. Alternatively, the recess, or at least one of the recesses and the electrically conductive material may have any other suitable shape, such as a substantially square or rounded cross-sectional shape in a plane parallel to the surface of the electrically insulating diamond material.

The at least one recess may be partially or entirely filled with the electrically conductive material. The electrically conductive material may have a surface at a level that substantially coincides with a level of the surface of the electrically insulating diamond material.

In one example the electrically conductive material is formed from a brazing alloy such as an active brazing alloy. The electrically conductive material may also be formed from another suitable material, such as a carbon-paste.

In an alternative embodiment the electrically conductive material comprises a conductive diamond material, such as a nitrogen or boron incorporated diamond material that may be poly-crystalline (for example nano-crystalline or micro-crystalline) or mono-crystalline.

The circuit board may be composed of a diamond material.

The at least one recess may be provided in the form of a groove or channel.

The conductive material in the at least one recess may have a thickness in a direction that is parallel to a plane of the surface of electrically insulating diamond material, the thickness being less than 100 µm, less than 50 µm or less than 10 µm.

The at least one recess may be one of a plurality of recesses in which the electrically conductive material is positioned. At least some of the recesses with the electrically conductive material may be joined. Further, at least some of the recesses with the electrically conductive material may be electrically insulated from one another.

The electrically conductive material may comprise surface mounting pads or bonding pads for mounting or bonding an electronic component to the circuit board.

The present invention provides in a second aspect an implantable medical device comprising the circuit board of the first aspect of the present invention.

The implantable medical device typically comprises a housing and the circuit board may form a portion of the housing. Further, the implantable medical device may comprise an electronic component that is positioned within an interior of the implantable medical device and is electrically coupled to the circuit board. The implantable medical device may be a retinal prosthesis.

The present invention provides in a third aspect a method of forming a circuit board, the method comprising:
  providing a substrate that comprises an electrically insulating diamond material; and
  forming an electrically conductive material, the electrically conductive material being formed so as to be located at least partially within a recess of the electrically insulating diamond material;
  wherein the recess extends into only a portion of a thickness of the electrically insulating diamond material from a surface of the electrically insulating diamond material.

It will be appreciated that the circuit board is formed such that the electrically conductive material within the at least one recess does not extend through to a surface of the electrically insulating diamond material opposite the surface on which the recess is provided. The electrically conductive material extends only partially into the thickness of the electrically insulating diamond material, for example up to 10%, 20%, 30%, 40%, 50%, 60%, 70%, 80% or 90% of the thickness of the electrically insulating diamond material.

Further, it will be appreciated that the circuit board may be formed such that the conductive material is contained such that conductive material of adjacent recesses do not contact at a region of the electrically insulating diamond material that lies beyond the adjacent recesses. For example, the conductive material may be contained entirely within the at least one recess.

The step of providing the substrate may comprise milling the at least one recess into the electrically insulating material. Milling may comprise use of a focused ion beam or a laser beam.

The at least one recess may be a groove or channel.

The step of forming the electrically conductive material may comprise applying a brazing alloy into at least a portion of the at least one recess and exposing the brazing alloy to heat treatment to form the electrically conductive material in the at least one recess.

The electrically conductive material may initially be formed such that a portion of the electrically conductive material projects beyond the surface of the substrate. The method may comprise the additional step of removing a portion of the electrically conductive material such that the electrically conductive material then has a surface level that approximates that of the surface of the substrate.

The method may also comprise growing a conductive diamond material within the at least one recess using chemical vapour deposition. The electrically conductive diamond material may be nitrogen or boron incorporated. The electrically conductive diamond material may be formed within the at least one recess and on at least a portion of the surface of the substrate. The method may comprise subsequently removing a portion of the electrically conductive diamond material such that a surface of the electrically conductive diamond material then has a level that approximates that of the electrically insulating diamond material.

DETAILED DESCRIPTION OF DRAWINGS

Embodiments of the present invention relate to a circuit board having a substrate comprising an electrically insulating diamond material and an electrically conductive material. The electrically conductive material extends into a portion of a thickness of the insulating diamond material.

In one embodiment the circuit board comprises a plurality of electrically conductive portions formed within recesses (such as groves, channels, or rounded or substantially square recesses) of an electrically insulating diamond substrate and arranged as electrical connections, such as bonding pads or interconnecting "wires" that are partially or entirely embedded within the insulating diamond material.

The electrically conductive portions do not penetrate through the electrically insulating diamond substrate, although it will be appreciated that the circuit board may be arranged such that it can be connected to an external data and/or power system, for example via a through hole interconnection or similar. In any event, in this example, the electrically conductive portions do not themselves penetrate through the electrically insulating diamond substrate.

Certain embodiments of the present invention may be particularly useful for medical applications such as devices implantable in biological tissue. However, a person skilled in the art will appreciate that embodiments of the present invention are suitable for a variety of different applications.

Forming the electrically conductive material may comprise applying a suitable brazing alloy, such as an active brazing alloy, or a carbon paste to recesses formed in the electrically insulating diamond material. Suitable heat treatment is used to complete formation of the materials. Alternatively, the electrically conductive materials may for example be provided in the form of conductive diamond materials. The formation of the electrically conductive materials will be described further below with reference to FIG. 5.

Figure 1:
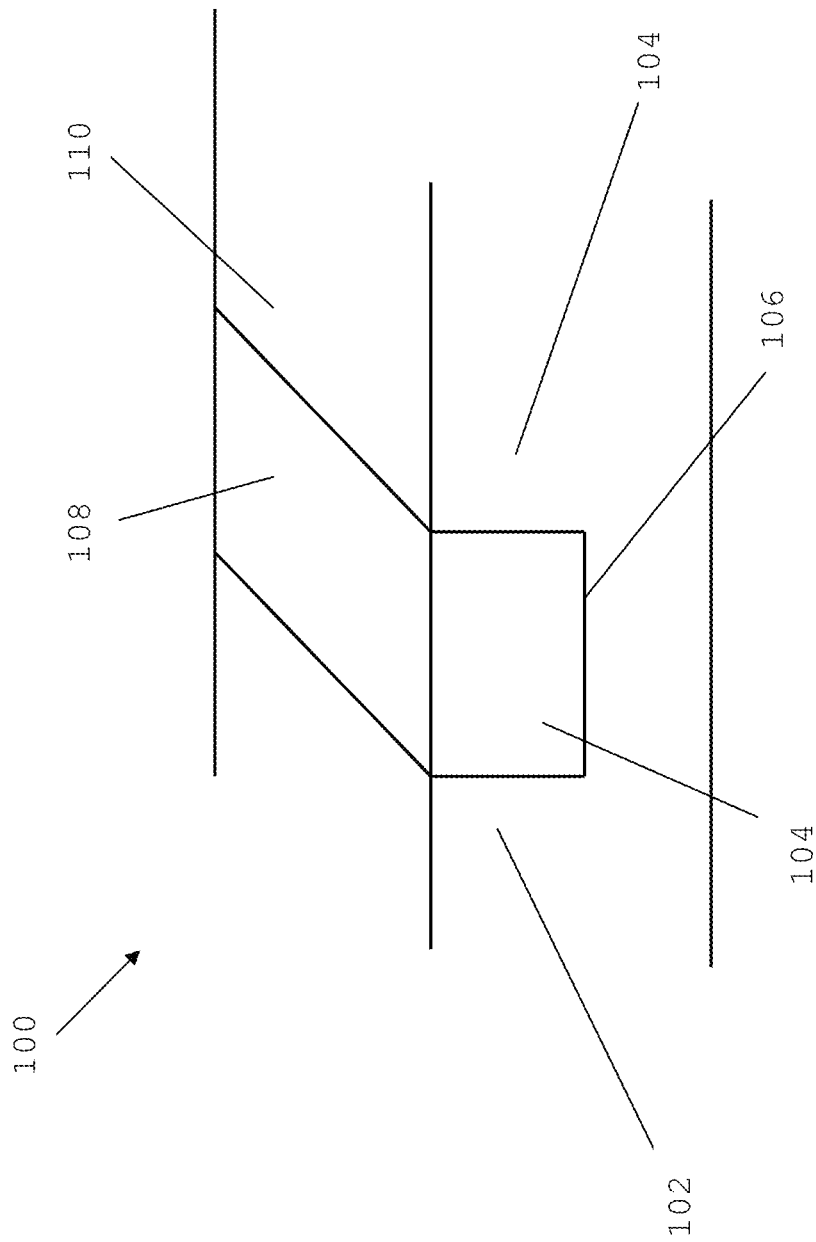
FIG. 1 is a perspective view of a portion of a circuit board according to an embodiment of the present invention.

Specific embodiments of the present invention will now be described in more detail. Referring to FIG. 1, there is shown a circuit board 100 comprising a substrate 102 of insulating diamond material, and a conductive portion 104 comprising an electrically conductive material. The conductive portion 104 is arranged in a correspondingly shaped recess 106 of the substrate 102. A surface 108 of the conductive portion 104 is flush with a surface 110 of the substrate 102. The conductive portion 104 comprises material capable of forming a relatively strong bond with the diamond material substrate 102.

A particularly strong bond between the substrate 102 and the conductive portion 104 can be formed if the conductive portion 104 also comprises diamond material, for example nitrogen or boron incorporated nano-crystalline diamond material. Thus the circuit board 100 may be made completely of diamond material, resulting in a biocompatible and robust circuit board that is impermeable to fluid ingress.

Figure 2:
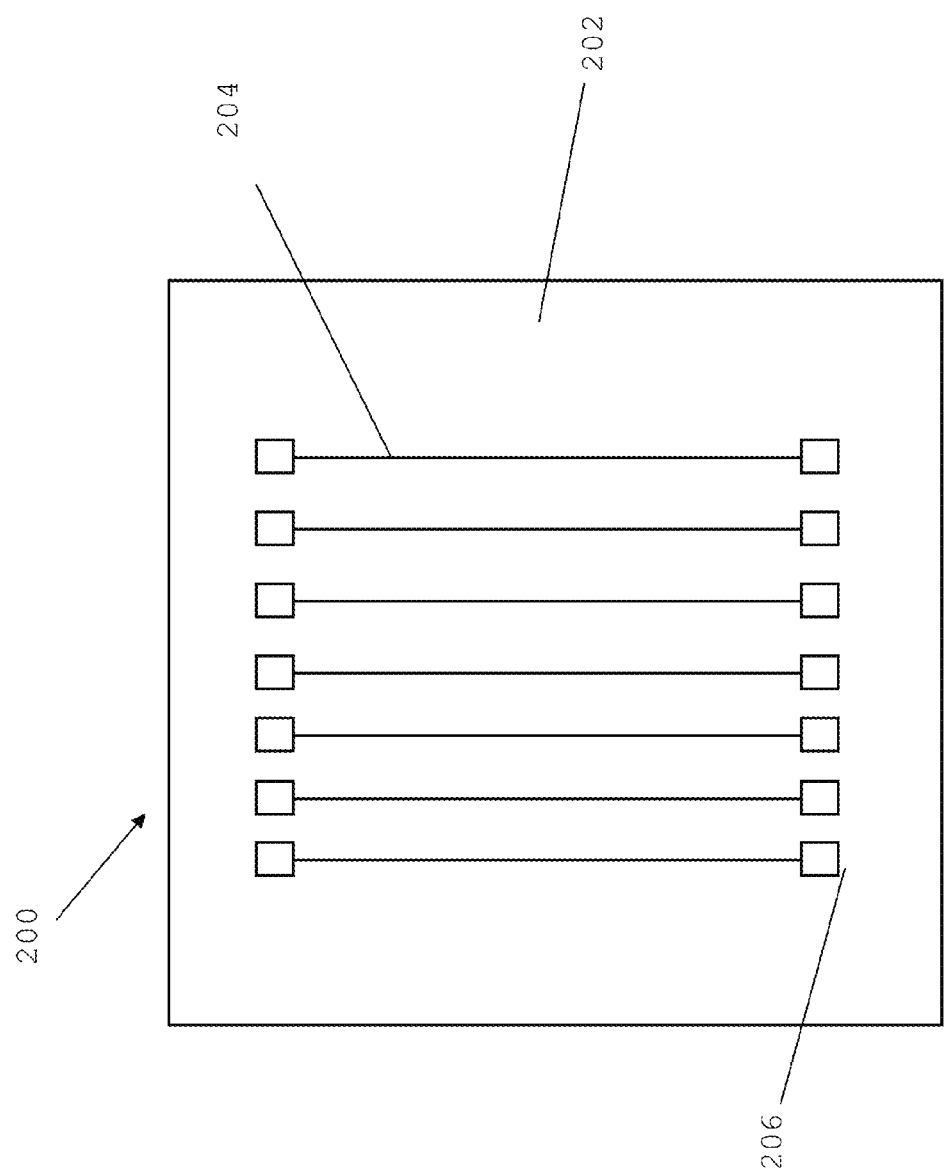
FIG. 2 is a plan view of a circuit board according to an embodiment of the present invention.

Referring now to FIG. 2, there is shown a circuit board 200 in accordance with a further embodiment of the present invention. The circuit board 200 comprises an insulating diamond substrate 202 and a plurality of conductive portions 204. The conductive portions 204 are elongate and provide interconnections between electronic components (not shown). Such interconnections may be as thin as 5 μm (in a direction parallel to a plane of the surface of the substrate 202), but may alternatively also have another suitable thickness, such as less than 100 μm, less than 50 μm or less than 10 μm.

Electrically conductive pads 206 for the mounting of components are disposed at each end of, and in contact with, the elongate conductive portions 204. The electrically conductive pads 206 may have a width, or a diameter if substantially circular in shape, in the order of 200 μm. Electronic components (not shown) may be placed in contact with the electrically conductive pads 206. In this embodiment, both the conductive pads 206 and the elongate conductive portions 204 extend into a thickness of the insulating diamond substrate 202, in a manner similar to that of the circuit board 100, and have a surface that is substantially flush with that of the substrate 202.

Figure 3:
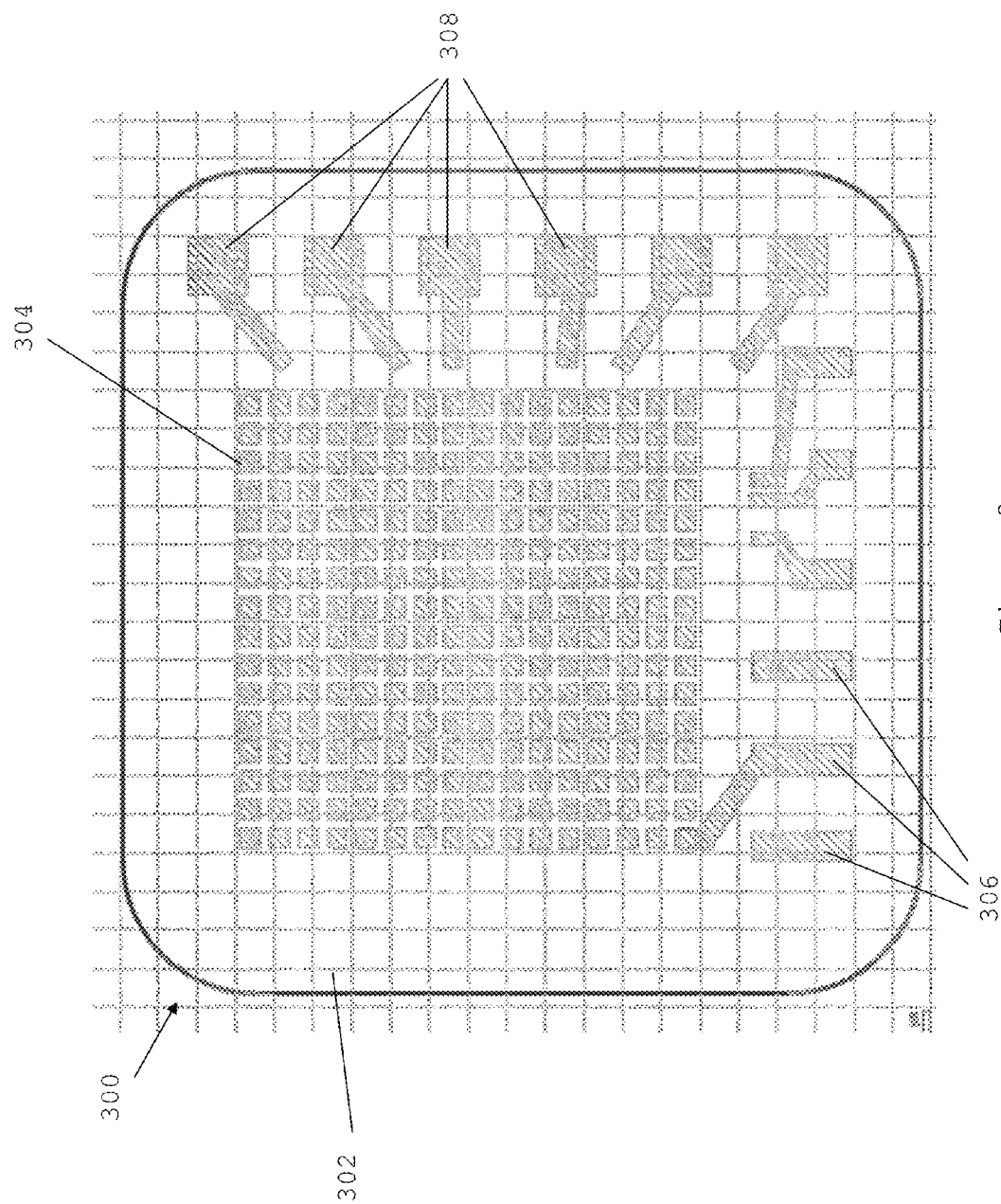
FIG. 3 is a plan view of a circuit board according to an embodiment of the present invention.

FIG. 3 illustrates another example circuit board 300 in accordance with an embodiment of the present invention. The circuit board 300 comprises an insulating diamond substrate 302 and a plurality of conductive portions 304, 306 and 308 of various shapes and sizes. Each of the conductive portions 304, 306 and 308 extend into a portion of the thickness of the substrate 302, and has a surface that is flush with a surface of the insulating diamond substrate 302. A person skilled in the art will appreciate that many alternative arrangements of the conductive portions 304, 306, 308 of the circuit board 300 are possible.

In the embodiment shown in FIG. 3, the electrically conductive portions 304 form a matrix of bonding pads. The electrically conductive portions 304 may be connected with, for example, a microprocessor (not shown). The electrically conductive portions 308 are arranged for surface mounting of further circuit components and the electrically conductive portions 306 are arranged for coupling to external data and power sources (not shown).

Figure 4:
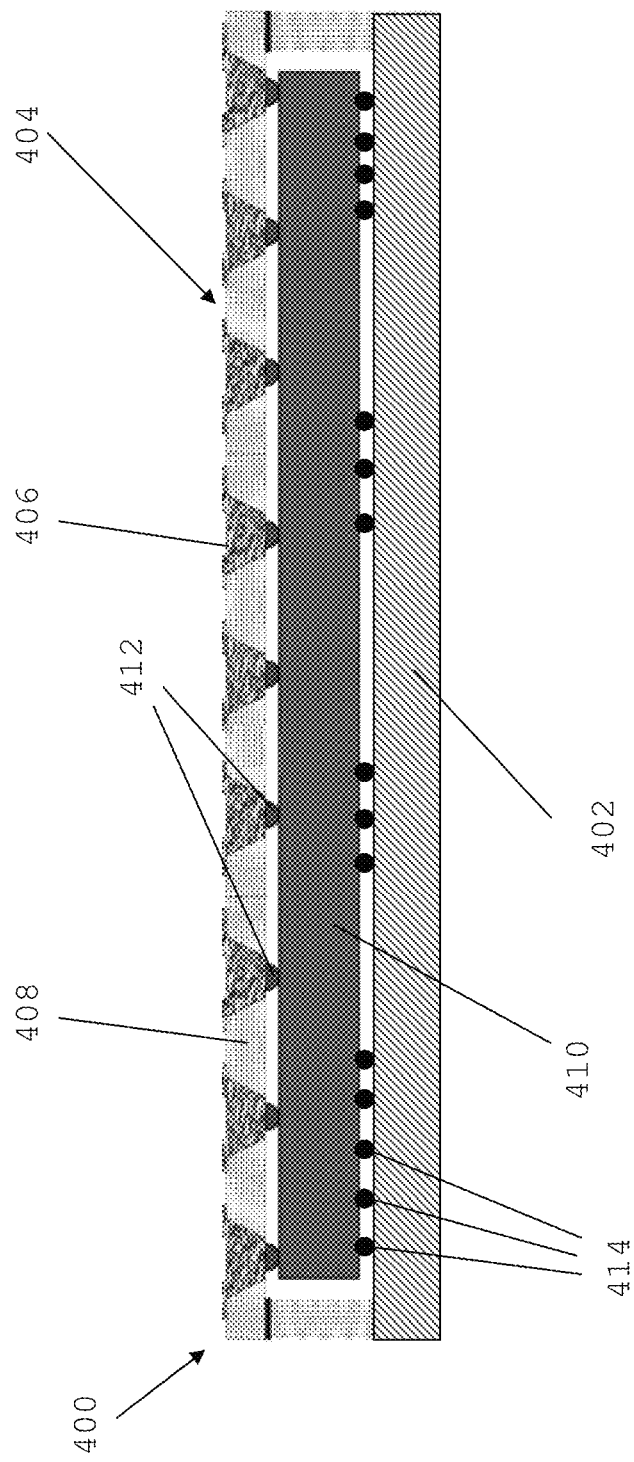
FIG. 4 is a cross-sectional view of a medical device in accordance with an embodiment of the present invention.

Referring now to FIG. 4, a medical device 400 in accordance with an embodiment the present invention will now be described. The medical device 400 comprises in this embodiment a circuit board 402, which is similar to the circuit board 300 described above with reference to FIG. 3. The medical device 400 is in this embodiment a retinal prosthesis arranged for implanting into the retina of a patient and for stimulating an inner cell layer of the retina. The implantable medical device 400 comprises an electrode array 404 that has a plurality of electrically conducting elements 406 and electrically insulating material 408 surrounding portions of the electrically conducting elements 406. In this embodiment, the electrically conducting elements 406 of the electrode array 404 form an array that can be positioned in contact with the retina of an eye and thus capable of stimulating retinal cells.

The electrically conducting elements 406 and the electrically insulating material 408 are composed of diamond material having different electrical properties. In this particular embodiment, the electrically conducting elements 406 are composed of nitrogen incorporated ultra nano-crystalline diamond material having $sp^2$ and $sp^3$ carbon bonds and the electrically insulating material 408 is composed of polycrystalline diamond material having primarily $sp^3$ carbon bonds.

The electrode array 404 forms a lid of a housing of the implantable medical device 400, and a stimulating face of the electrode array 404 is exposed. The housing encases a microprocessor chip 410 that is arranged to control stimulating signals conducted via electrical bonds 412 through the conducting elements 406 of the electrode array 404 to stimulate retinal cells. Conductive pads 414 of the microprocessor 410 are electrically coupled to conductive portions of the control circuit 402 by microfabrication methods such as flip chip bonding. Further, external components (not shown) such as power supplies can be electrically coupled to the microprocessor 410 via the circuit board 402.

A person skilled in the art will appreciate that the circuit board in accordance with embodiments of the present invention may be used for a variety of implantable medical devices other then retinal implants. Further, the circuit board in accordance with embodiments of the present invention may be used for devices other then implantable devices.

Figure 5:
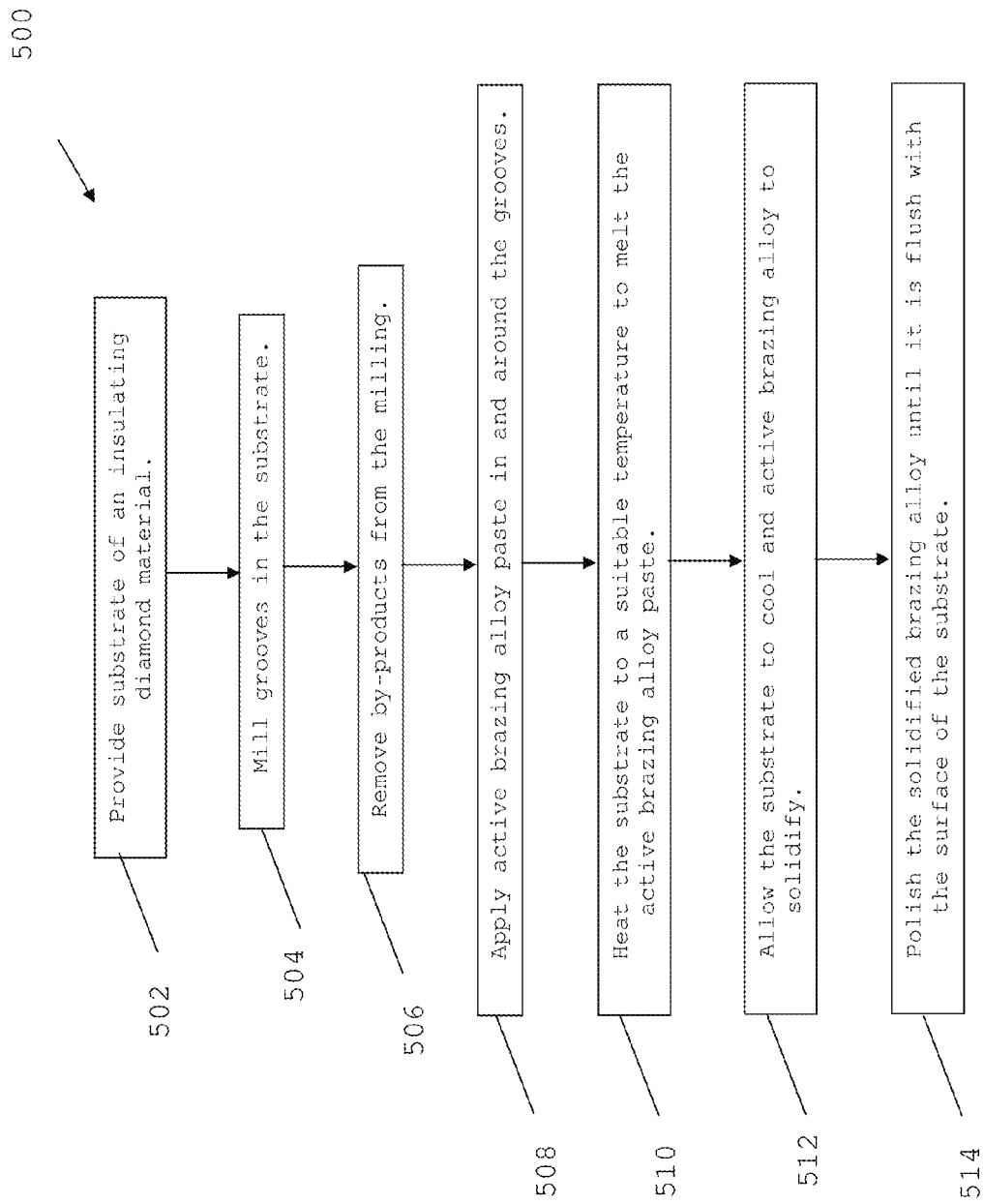
FIG. 5 is a flow chart of a method of forming a circuit board according to an embodiment of the present invention.

Referring now to FIG. 5, a method 500 of forming a circuit board according to an embodiment of the present invention will now be described.

The method 500 comprises an initial step 502 of providing a substrate of a diamond material. In step 504, grooves are milled into the substrate using a laser or a focused ion beam. For example, a diode pumped solid state laser with a wavelength of 532 nm may be used. Laser or focused ion beam milling typically results in the excavated material remaining in and around the milled area of interest, which is removed in step 506 using acid boil etching or a hydrogen plasma treatment.

Once the excavated material has been removed, an active brazing alloy paste is applied in step 508 into the grooves and also around the grooves to optimise filling of the grooves. In step 510, the substrate with the active brazing alloy paste is heated to a suitable temperate (such as a temperature of approximately 900° C.) so that the active brazing alloy melts and completely fills the grooves. The heating step 510 will typically be performed under vacuum. The active brazing alloy is then allowed to cool in step 512 and, in step 514, the solidified brazing alloy is then polished until it has a surface that has a level that approximates that of the substrate.

The active brazing alloy may, for example, comprise silver, gold, titanium, vanadium or chromium. As mentioned above, the conductive materials may alternatively be provided in other suitable forms. For example a carbon paste or a suitable soldering paste may be used in a manner similar to the active brazing material.

In an alternative embodiment the conductive material is provided in the form of a diamond material in which a suitable other material has been incorporated. In this particular embodiment, the electrically conductive material is composed of nitrogen incorporated ultra nano-crystalline diamond material having $sp^2$ and $sp^3$ carbon bonds. The electrically conductive diamond material is formed on the insulating diamond substrate. Using a gas mixture of Argon (Ar, 70-94%), methane ($CH_4$, 1-5%) and Nitrogen ($N_2$, 5-20%), a layer of nitrogen incorporated ultra nano-crystalline diamond having a suitable thickness is formed in the grooves of the insulating diamond substrate and on remaining surface portions of the substrate. After growth of the conductive diamond material the substrate with the conductive diamond material is polished until the conductive diamond material has a surface that is flush with a surface of the insulating diamond material.

A person skilled in the art will appreciate that there are other methods of producing the circuit board. For example, a mask having suitably shaped apertures may be placed over the substrate before filling the grooves with conductive material. Subsequent polishing may or may not be necessary.

Although the invention has been described with reference to particular examples, it will be appreciated by those skilled in the art that the invention may be embodied in many other forms.

The invention claimed is:

1. A diamond circuit board comprising:
   an electrically insulating diamond material having a surface;
   at least one recess extending into only a portion of a thickness of the electrically insulating diamond material from the surface of the electrically insulating diamond material such that only the electrically insulating diamond material defines the recess; and
   an electrically conductive material located at least partially within the recess on the electrically insulating diamond material that defines the recess.

2. The diamond circuit board of claim 1, wherein the at least one recess extends along a length of the surface of the electrically insulating diamond material.

3. The diamond circuit board of claim 1, wherein the recess, or at least one of the recesses, and the electrically conductive material are elongated.

4. The diamond circuit board of claim 1, wherein the recess, or at least one of the recesses and the electrically conductive material have a substantially square or rounded cross-sectional shape in a plane parallel to the surface of the electrically insulating diamond material.

5. The diamond circuit board of claim 1, wherein the at least one recess is partially filled with the electrically conductive material.

6. The diamond circuit board of claim 1, wherein the at least one recess is entirely filled with the electrically conductive material.

7. The diamond circuit board of claim 1, wherein the electrically conductive material has a surface at a level that substantially coincides with a level of the surface of the electrically insulating diamond material.

8. The diamond circuit board of claim 1, wherein the electrically conductive material is formed from a brazing alloy.

9. The diamond circuit board claim 1, wherein the electrically conductive material is formed from a carbon-paste.

10. The diamond circuit board of claim 1, wherein the electrically conductive material comprises a conductive diamond material.

11. The diamond circuit board of claim 10, wherein the conductive diamond material is a nitrogen or boron incorporated diamond material.

12. The diamond circuit board of claim 10, wherein the circuit board is composed of a diamond material.

13. The diamond circuit board of claim 1, wherein the at least one recess is provided in the form of a groove or channel.

14. The diamond circuit board of claim 1, wherein the at least one recess is one of a plurality of recesses in which the electrically conductive material is positioned.

15. The diamond circuit board of claim 1 wherein the electrically conductive material comprises surface mounting pads or bonding pads for mounting or bonding an electronic component to the circuit board.

16. An implantable medical device comprising:
a diamond circuit board comprising:
an electrically insulating diamond material having a surface;
at least one recess extending into only a portion of a thickness of the electrically insulating diamond material from the surface of the electrically insulating diamond material such that only the electrically insulating diamond material defies the recess such that only the electrically insulating diamond material defines the recess;
an electrically conductive material located at least partially within the recess on the electrically insulating diamond material that defines the recess;
a housing;
an electronic component, wherein the circuit board forms a portion of the housing and the electronic component is positioned within an interior portion of the implantable medical device and is coupled to the circuit board.

17. A method of forming a diamond circuit board, the method comprising:
providing a substrate that comprises an electrically insulating diamond material; and
forming an electrically conductive material, the electrically conductive material being formed so as to be located at least partially within a recess of the electrically insulating diamond material, the recess being defined only by the electrically insulating diamond material;
wherein the recess extends into only a portion of a thickness of the electrically insulating diamond material from a surface of the electrically insulating diamond material and the electrically conductive material is located on the electrically insulating diamond material that defines the recess.

18. The method of claim 17, wherein the step of providing the substrate comprises milling the at least one recess into the electrically insulating material and wherein the at least one recess is a groove or channel.

19. The method of claim 17, wherein the step of forming the electrically conductive material comprises applying a brazing alloy into at least a portion of the at least one recess and exposing the brazing alloy to heat to form the electrically conductive material in the at least one recess.

20. The method of claim 17, wherein forming the electrically conductive material comprises growing a conductive diamond material using chemical vapour deposition.

\* \* \* \* \*